(12) United States Patent
Thürlemann et al.

(10) Patent No.: US 8,465,635 B2
(45) Date of Patent: Jun. 18, 2013

(54) SYSTEM FOR DIFFERENTIAL DETERMINATION OF A PROTEOLYTIC ENZYME LEVEL IN A BODILY FLUID

(75) Inventors: Charles Thürlemann, Egnach (CH); André Haeberli, Gümligen (CH); Erik Jan Frenkel, Neuchâtel (CH)

(73) Assignee: Asulab S.A., Marin (CH)

( * ) Notice: Subject to any disclaimer, the term of this patent is extended or adjusted under 35 U.S.C. 154(b) by 1376 days.

(21) Appl. No.: 11/482,130

(22) Filed: Jul. 7, 2006

(65) Prior Publication Data

US 2007/0009982 A1    Jan. 11, 2007

(30) Foreign Application Priority Data

Jul. 7, 2005    (EP) .................................... 05014751

(51) Int. Cl.
*G01N 27/327*    (2006.01)
(52) U.S. Cl.
USPC ................................ 204/403.01; 204/403.04
(58) Field of Classification Search
USPC ...................... 204/403.01–403.15; 205/777.5, 205/778, 792; 600/345–348
See application file for complete search history.

(56) References Cited

U.S. PATENT DOCUMENTS

| | | | |
|---|---|---|---|
| 4,303,853 A | 12/1981 | Thalmann | |
| 5,154,082 A | 10/1992 | Mintz | |
| 5,302,348 A | 4/1994 | Cusack et al. | |
| 5,320,732 A * | 6/1994 | Nankai et al. | ............. 204/403.04 |
| 5,378,628 A | 1/1995 | Gratzel et al. | |
| 5,856,195 A * | 1/1999 | Charlton et al. | ................ 436/50 |
| 6,066,504 A | 5/2000 | Jinn | |
| 6,129,823 A * | 10/2000 | Hughes et al. | ............. 204/403.1 |
| 6,168,699 B1 * | 1/2001 | Frenkel et al. | ........... 204/403.14 |
| 6,299,757 B1 * | 10/2001 | Feldman et al. | ............... 205/775 |

(Continued)

FOREIGN PATENT DOCUMENTS

| | | |
|---|---|---|
| EP | 0 471 986 A2 | 2/1992 |
| EP | 1 031 830 A1 | 8/2000 |

(Continued)

OTHER PUBLICATIONS

Thürlemann, Charles Bernard, "Entwicklung eines Biosensor-Systems für ein Patienten-Selbstmanagement der Behandlung mit Vitamin K-Antagonisten," University of Basel, 2005.

(Continued)

*Primary Examiner* — Luan Van
*Assistant Examiner* — Gurpreet Kaur
(74) *Attorney, Agent, or Firm* — Griffin & Szipl, P.C.

(57) ABSTRACT

The system includes: an assortment (10) of sensors (10*a*, 10*b*, 10*c*), wherein the working electrode (14*a*) of each sensor is covered with a specific reagent of a given proteolytic enzyme, including a substrate capable of releasing leaving groups (LG) via the action of the enzyme; a measuring apparatus (20) having an electronic circuit imposing a current, whose intensity or voltage may or may not be variable, between the electrodes, and for receiving in return a signal representative of the release of the LG; and an electronic apparatus (30) for processing the transmitted signal and displaying, on a display screen (32), an indication representative of the release of the LG as a function of time. The system may be used to determine, in a plasma or whole blood sample, factors responsible for a coagulation anomaly.

21 Claims, 4 Drawing Sheets

U.S. PATENT DOCUMENTS

| | | | |
|---|---|---|---|
| 6,352,630 B1 * | 3/2002 | Frenkel et al. | 204/403.02 |
| 6,352,853 B1 | 3/2002 | King et al. | |
| 6,495,336 B1 | 12/2002 | Ludin et al. | |
| 6,558,320 B1 * | 5/2003 | Causey et al. | 600/300 |
| 7,476,827 B1 * | 1/2009 | Bhullar et al. | 219/121.69 |
| 2004/0200721 A1 | 10/2004 | Bhuller et al. | |

FOREIGN PATENT DOCUMENTS

| | | |
|---|---|---|
| EP | 0 679 193 B1 | 8/2001 |
| JP | 2004-101514 A | 4/2004 |
| WO | 94/16095 | 7/1994 |
| WO | 00/33074 | 6/2000 |
| WO | 03/093831 A1 | 11/2003 |

OTHER PUBLICATIONS

European Search Report issued in corresponding application No. EP 05 01 4751, completed Feb. 27, 2006.

Webster's New Collegiate Dictionary (1977), pp. 68, 1279 and 1294.

* cited by examiner

SYSTEM FOR DIFFERENTIAL DETERMINATION OF A PROTEOLYTIC ENZYME LEVEL IN A BODILY FLUID

This application claims priority from European Patent Application No. 05014751.1, filed Jul. 7, 2005, the entire disclosure of which is incorporated herein by reference.

FIELD OF THE INVENTION

The invention concerns a system for implementing a test for the differential determination in real time of the evolution of a proteolytic enzyme level in a small bodily fluid sample, and as a function of this dynamic differential analysis, for anticipating the tendency of a patient to develop a given pathology.

The invention will be more particularly illustrated by the endogenous thrombin potential test (ETP), wherein the continuous measurement of certain plasmatic coagulation factors allows abnormal levels to be detected and forestall, via an appropriate treatment, a risk of haemophilia, or conversely, thrombosis.

The invention also concerns a laboratory system, which could be adapted to take the measurements at the patient's bedside.

BACKGROUND TO THE INVENTION

Finding out the blood coagulation time, designated as prothrombin time (PT), i.e. the aptitude of different proteolytic enzymes, also known as "factors", to contribute to the formation of a clot, or conversely, to prevent it, forms part of routine examinations, or even daily examinations in numerous acquired, traumatic, pre or post-operative pathological situations. It is, for example, necessary, during anticoagulant treatment for heart disease, to be able to adjust the dosage of an anti-thrombotic medicine, for example warfarin or heparin, in order to prevent any risk of haemorrhagy in the event of an overdose, or conversely, the risk of thrombosis if the anticoagulant dose is insufficient.

This determination of prothrombin time (PT) or partially activated thromboplastin time (APPT) has long been carried out in a laboratory by direct visual observation of the time necessary for a clot to form, then with the help of more or less complex and cumbersome apparatus usually relying upon optical detection, such as those disclosed for example in U.S. Pat. Nos. 5,302,348 and 5,154,082.

According to most recent methods, the principle consists in using a chemical substrate incorporating at least one chemical reactant, an end link of which can be cut by a specific enzyme to release a group (LG) whose presence can be detected in the measuring medium by a signal representative of the enzyme activity.

This method of detection corresponds for example to that disclosed in EP Patent No. 0 679 193. In the method disclosed, a sensor includes a chemical substrate, an end link of which can be cut by the enzyme being analysed to release a group (LG) whose concentration representative of activity of the enzyme in the medium can be measured by optical means based on alterations in colorimetry, luminescence or fluorescence. When the bodily fluid being analysed is whole blood, the red blood cells have to be removed, either by prior centrifugation of the sample, or by providing a membrane forming a barrier to the red blood cells on the sensor. This method thus has the drawback of requiring a relatively long, even expensive analysis time, to remove the red blood cells.

The aforementioned drawback can be greatly reduced, even removed, with the method proposed in EP Patent No. 1 031 830 and in U.S. Pat. No. 6,352,630 B1, both of which are incorporated in this Application by reference. The method, which concerns the blood coagulation measurement time, also relies on the indirect determination of the activity of a proteolytic enzyme by means of a chemical substrate able to release, via the action of the enzyme, leaving groups which will alter the electric properties of the medium, the resulting signal being in this case analysed by amperometry and correlated with a PT or APTT value representative of the coagulation time. With this non-colorimetric method, the prior preparation to obtain clear plasma is omitted, and determination can be carried out more quickly on whole blood.

All of the methods that have just briefly been recalled only allow an overall determination to be carried out and do not identify, among all the enzymes involved in the coagulation phenomenon, the enzyme responsible for a coagulation anomaly, whether this be haemophilia or thrombosis.

Until recent times, in order to obtain this kind of information, the method consisted in separating a blood sample into several samples and causing reactions with various anti-bodies to identify which enzyme was defective. This method required a relatively large blood sample, necessitated a lot of time and could only be carried out in a laboratory.

More recently, International Patent Application No. WO 03/093831 discloses a method for determining in real time the evolution of thrombin activity in a blood sample, but preferably in a plasma sample, relying upon fluorometric determination, compared to a calibration curve. This method has the same drawbacks as those previously cited for overall prothrombin time determination, concerning in particular the relatively large volume of the sample (approximately 160 μl, 80 μl of which is for the calibration solution), and the rather long measuring time (approximately 45 minutes).

SUMMARY OF THE INVENTION

It is thus an object of the present invention to overcome the drawbacks of the aforecited prior art by providing a differential determination test of the evolution of a proteolytic enzyme over time and particularly to perform a kind of screening of the activity of the enzymes involved in the coagulation phenomenon in a sample of whole blood or a small volume of plasma, and in a relatively short time.

The invention therefore concerns a system for electrochemically determining the evolution of the concentration or activity of at least one proteolytic enzyme to detect any deficiency thereof or abnormal activity in a small sample of bodily fluid, such as plasma or whole blood.

The system includes an assortment of electrochemical sensors, a measuring apparatus and an electric signal processing apparatus.

Each sensor has the shape of a tongue of small dimensions carrying at least one reference electrode and one working electrode on which a specific reactant for a given proteolytic enzyme is immobilised, whose composition incorporates at least one chemical substrate, an end link of which can be cut by the enzyme to release leaving groups (LG).

The measuring apparatus includes at least one connection slot for receiving a sensor, and an electronic circuit powered by an energy source for imposing an electric current between the electrodes of the sensor whose intensity or voltage may or may not be variable, and receiving in return an electric signal representative of the release of the leaving groups (LG).

In a preferred embodiment, the measuring apparatus allows chrono-amperometric determination to be carried out.

The electronic apparatus includes software for processing the signal emitted by the measuring apparatus and displaying an indication representative of the release of leaving groups (LG) over time on a display screen. This data can be given on the screen in alphanumerical form, or in the form of curves displayed sequentially or in a mosaic.

Thus, in accordance with a first embodiment of the present invention, a system for the electrochemical determination of the evolution of the concentration or activity of at least one proteolytic enzyme for detecting a deficiency or abnormal activity thereof in a small sample of bodily fluid is provided, wherein the system includes: (a) an assortment of electrochemical sensors, each having the shape of a tongue of small dimensions carrying at least one reference electrode and one working electrode on which a specific reagent for a given proteolytic enzyme is immobilised, and the composition of which includes at least one chemical substrate, an end link of which can be cut by the enzyme to release leaving groups; (b) a measuring apparatus including at least one connecting slot for receiving a sensor and whose electronic circuit, powered by an energy source, imposes, between the electrodes of the sensor, an electric current whose intensity or voltage may or may not be variable, and for receiving in return an electric signal representative of the release of the leaving groups, and (c) an electronic apparatus including software for processing the signal transmitted by the measuring apparatus to display on a display screen an indication representative of the release of the leaving groups as a function of time. In accordance with a second embodiment of the present invention, the first embodiment is modified so that the electronic circuit of the measuring apparatus is arranged for carrying out a chronoamperometric determination. In accordance with a third embodiment of the present invention, the third embodiment is modified so that each assortment of sensors is made up of several sensors, each having a specific reagent for a given proteolytic enzyme, wherein the measuring apparatus can include as many connecting slots as there are sensors in an assortment and in that the electronic apparatus software can differentiate the sensors to display curves sequentially or in a mosaic. In accordance with a fourth embodiment of the present invention, the first embodiment is modified so that each sensor of an assortment includes a material mark corresponding to the determination of a specific enzyme, wherein the mark on the sensor is complementary to a material mark on the connection with the measuring apparatus. In accordance with a fifth embodiment of the present invention, the first embodiment is modified so that the assortment of electrochemical sensors also includes a calibration sensor.

In accordance with a sixth embodiment of the present invention, the first embodiment is modified so that the measuring apparatus further includes a closing device for insulating the sensors inserted into the apparatus from the external medium, and a thermoregulation device for keeping the sensors at a determined constant temperature during the entire measurement. In accordance with a seventh embodiment of the present invention, the first embodiment is modified so that the measuring apparatus further includes a thermal probe for measuring the ambient temperature and in that the electronic apparatus software enables the reference curve to be selected as a function of the ambient temperature. In accordance with an eighth embodiment of the present invention, the first embodiment is modified so that the measuring apparatus further includes a secondary display screen for displaying an overall or instantaneous parameter of the measurement that is carried out. In accordance with a ninth embodiment of the present invention, the eighth embodiment is further modified so that the displayed parameter is the prothrombin time or the activated partial thromboplastin time when the bodily fluid is plasma or whole blood.

In accordance with a tenth embodiment of the present invention, the first embodiment is modified so that the measuring apparatus and the electronic apparatus are united in a single operating unit. In accordance with an eleventh embodiment of the present invention, the first embodiment is modified so that the volume of the sample of bodily fluid taken is less than 10 µl. In accordance with a twelfth embodiment of the present invention, the first embodiment is modified so that it displays an indication of the measurement carried out on the display screen in graphic or other form. In accordance with a thirteenth embodiment of the present invention, the first embodiment is modified so that the biological fluid is blood, particularly whole blood, in which the evolution of the concentration of coagulation factors or conversely coagulation inhibitors is determined to detect any deficiency, or conversely an excess, or abnormal activity. In accordance with a fourteenth embodiment of the present invention, the twelfth embodiment is further modified so that the composition of the specific reagent includes at least one oligopeptide substrate, an end link of which can be separated by a coagulation factor to give a leaving group, a thromboplastin and a buffer medium.

BRIEF DESCRIPTION OF THE DRAWINGS

Other features and advantages of the present invention will appear more clearly upon reading the following description of an example embodiment, given by way of non-limiting illustration, with reference to the annexed drawings, in which:

FIG. 1A shows a sensor variant;

DETAILED DESCRIPTION OF THE INVENTION

Figure 1:
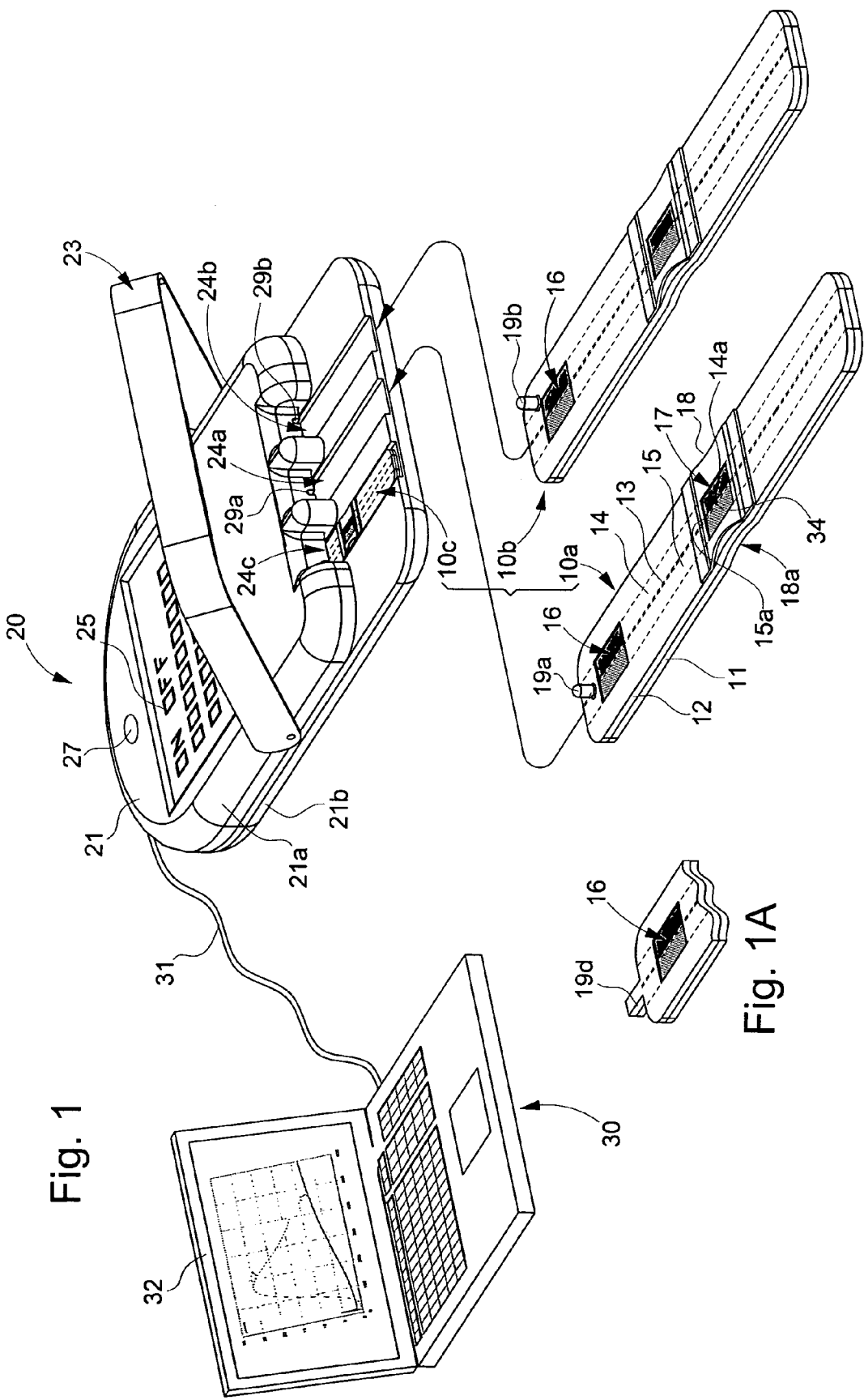
FIG. 1 shows in perspective a measuring system according to the invention.

Referring first of all to FIG. 1, a system according to the invention is shown by way of example for screening a patient's blood, possibly at his bedside. The system includes an assortment 10 of electrochemical sensors, a measuring apparatus 20 and an electronic apparatus 30, these three elements not being shown on the same scale.

In the example shown, assortment 10 includes three sensors 10a, 10b and 10c shown for convenience on a larger scale. Each sensor has the shape of a tongue approximately 40 mm long and 8 mm wide.

Referring more particularly to sensor 10a, which is, for example, for detecting a prothrombin deficiency (also called factor II), it can be seen that it includes a thin plastic support 11, made for example of PET, carrying two current collectors 14, 15, over its entire length, separated by a small space 13 which insulates them electrically.

Support 11 and collectors 14, 15 are covered with an insulating coating 12 in which two apertures 16, 17 are cut, for example by stamping, close to each end and making visible portions of collectors 14, 15. A first aperture 16 electrically connects sensor 10*a* to measuring apparatus 20. The second aperture 17 forms the measuring zone, the visible portions of the collectors respectively forming the working electrode 14*a* and the reference electrode 15*a*.

Working electrode 14*a* is made for example by laminating a thin strip of platinum and reference electrode 15*a* is made by laminating a thin strip of silver that is previously or subsequently chlorinated. It is also possible to provide a counter-electrode in the measuring zone. Working electrode 14*a* is coated with a specific reagent 34 described in detail hereinafter.

In the sensor model shown, it can be seen that measuring aperture 17 is covered with a transparent cap 18, forming a transverse capillary channel 18*a* for bringing the blood sample to be analysed into contact with electrodes 14*a* and 15*a*.

It can be seen that the end of the sensor includes a specific marking 19 of a sensor type from the assortment, enabling measuring apparatus 20 to "recognise" it. For sensor 10*a*, this marking is formed by a raised portion 19*a* located along the axis of the sensor. For sensor 10*b*, this raised portion 19*b* is offset to the right and for sensor 10*c*, shown in place in measuring apparatus 20, the raised portion 19*c* (not shown) is offset to the left. It is also possible to envisage other types of marking, for example a small extension 19*d* of the end of the sensor, as shown in FIG. 1A, or conversely, a small notch (not shown). The advantage of these marking means will appear more clearly with the description of measuring apparatus 20.

It will also be observed that assortment 10 can include a larger number of sensors, advantageously including a calibration sensor.

Measuring apparatus 20 includes a case 21 constructed by assembling two moulded plastic shells 21*a*, 21*b*, the bottom shell 21*b* extending slightly beyond top shell 21*a*. These two shells delimit a housing for an energy source and for an electronic circuit (not shown) for processing signals transmitted by the leaving groups (LG). This electronic circuit is an adaptation of the circuits used for dosing glucose, for example by amperometry as disclosed in U.S. Pat. No. 5,378, 628. It differs only in the different setting of the electric signal representative of the release of groups LG by the thrombin, or by other proteolytic enzymes.

Measuring apparatus 20 also includes as many connecting slots 24*a*, 24*b*, 24*c* as there are sensors 10*a*, 10*b*, 10*c* in the measuring system assortment. These connecting slots are made between and in shells 21*a* and 21*b* forming case 21. In the embodiment shown, the top shell has a notch and the bottom shell a hollow groove for inserting and removing the disposable sensor after use.

According to the embodiment shown, measuring apparatus 20 further includes a cap 23 that can be folded back and which insulates the sensors 10*a*, 10*b*, 10*c* introduced into the apparatus, which then includes a thermostat (not shown) for keeping the measuring zone at a constant temperature (for example 37° C.). As will be seen hereinafter, temperature has a very great influence on the generation of thrombin. Alternatively, it would be possible to omit a thermostated chamber by providing a probe (not shown) for measuring the ambient temperature and selecting a calibration curve from a group of curves, stored in the memory of the measuring apparatus, or even better in the electronic apparatus, as a function of various temperatures.

It will also be observed that each connecting slot 24*a*, 24*b*, and 24*c* includes a notch 29*a*, 29*b* and 29*c* (not visible) complementary to each raised mark 19*a*, 19*b* and 19*c*, i.e. preventing any inversion of the sensor and clearly designating, without any error, the curve or the data which will be displayed on the display screen.

With the type of marking shown in FIG. 1A, "recognition" of a determined sensor can be carried out by electronic means by measuring apparatus 20, such that any connecting slot can receive any sensor. This type of marking also increases the number of different sensors that an assortment 10 can include. For example, with a number of extensions 19*d* comprised between zero and 3 able to occupy three different positions, eight sensors can be differentiated.

It will be observed finally that measuring apparatus 20 could include a secondary display 25, able to serve as a screen for checking proper operation, for example by displaying ON or OFF depending upon whether control button 17 has been pressed or not, or by providing visual end of measurement data, enabling the sensors to be removed in complete security. The secondary display can also display, by way of complementary data, an overall measurement value, such as PT or APTT.

The measuring apparatus 20 that has just been described includes three connecting slots 24*a*, 24*b* and 24*c*, but it is clear that it could include a larger number, to enable a larger number of simultaneous measurements to be carried out.

Measuring apparatus 20 can be connected via a cord 31 to an electronic apparatus 30 including a display screen 32. In the example shown, the electronic apparatus is a portable computer, in which software for processing the signals received from measuring apparatus 20 has been installed, for displaying curves or data regarding the measurement being carried out on screen 32. The computer also enables the practitioner to store data useful to him for interpreting the curves, and/or enabling him to follow the pathology of a given patient, and to carry out the ordinary tasks possible with a computer.

In the example of FIG. 1, measuring apparatus 20 and electronic apparatus 30 are shown as separate elements, but it is entirely conceivable to unite them in a single operating unit. It is even possible to design the assembly in the form of a briefcase including a housing for storing sensor assortments 10.

Figure 2:
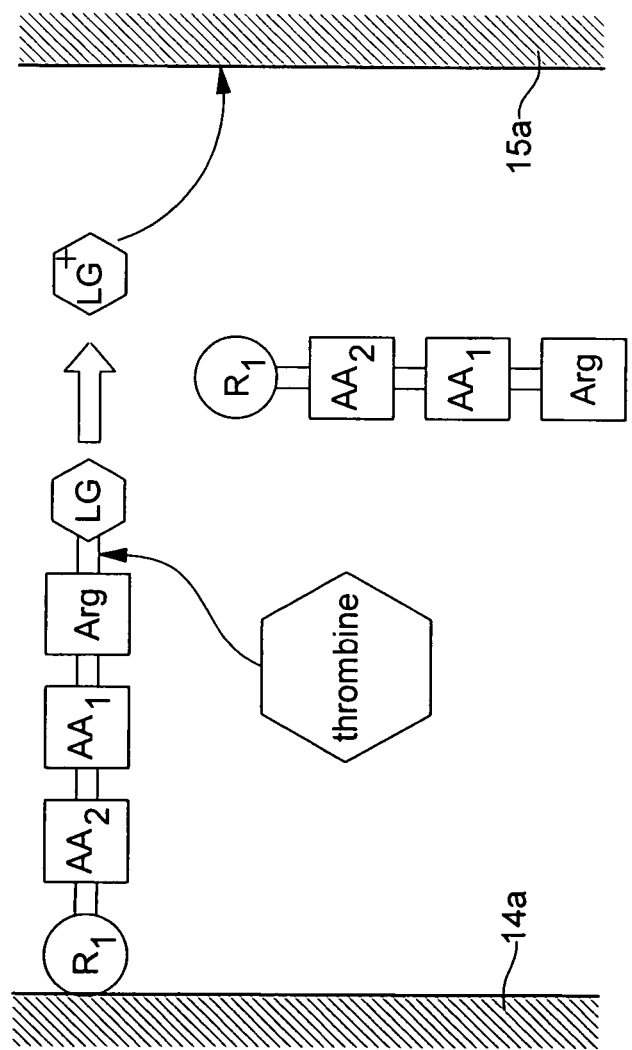
FIG. 2 is a diagram of the process leading to a signal that can be exploited by the measuring apparatus, then by the software of the electronic apparatus.

FIG. 2 is a schematic diagram of the reaction that generates a current between electrodes 14*a* and 15*a*, which are connected via an electronic detection circuit that is not shown. The substrate is represented schematically by the formula $R_1\text{-}AA_2\text{-}AA_1\text{-}Arg\text{-}LG$ in which $AA_1$ and $AA_2$ represent amino-acids such as those described in U.S. Pat. No. 4,303, 853 or 6,352,853, but it is entirely possible to use other peptides. Group $R_1$ represents a group connecting with working electrode 14*a* for orienting the oligopeptide and LG represents a leaving group, such as one of the groups described in the aforecited U.S. Pat. No. 6,352,853. In the left part of the diagram, it can be seen that the thrombin enzyme selectively cuts the connection between the arginine and the leaving group LG. In the right part of the diagram, it can be seen that the released leaving group can migrate towards electrode 15*a* and generate a current that will be proportional to the number of released leaving groups LG and thus to the quantity of thrombin formed in the medium per unit of time. In other words, determination of the activity of a given proteolytic enzyme relies on a chrono-amperometric measurement for tracing a curve representing the variation in intensity in $\mu A/cm^2$ over time expressed in seconds as shown in the graphs of FIGS. 3 to 6. This chrono-amperometric determination also allows, by means of an appropriate calculation algorithm, the measuring results to be displayed, for example in ETP value (endogenous thrombin potential).

In the method concerning an overall determination (PT or APPT), the retained value is for example that of the inflexion point, measured approximately in the 15 seconds following the start of the reaction and this value only represents around 10% of the total thrombin. With the test according to the invention, the reaction time is considerably longer, able to reach up to 45 min, preferably between 2 and 30 min and particularly between 3 and 10 min. This takes account of important parameters for the practitioner concerning the thrombin generating "dynamics" as explained in more detail with reference to FIG. 3.

Figure 3:
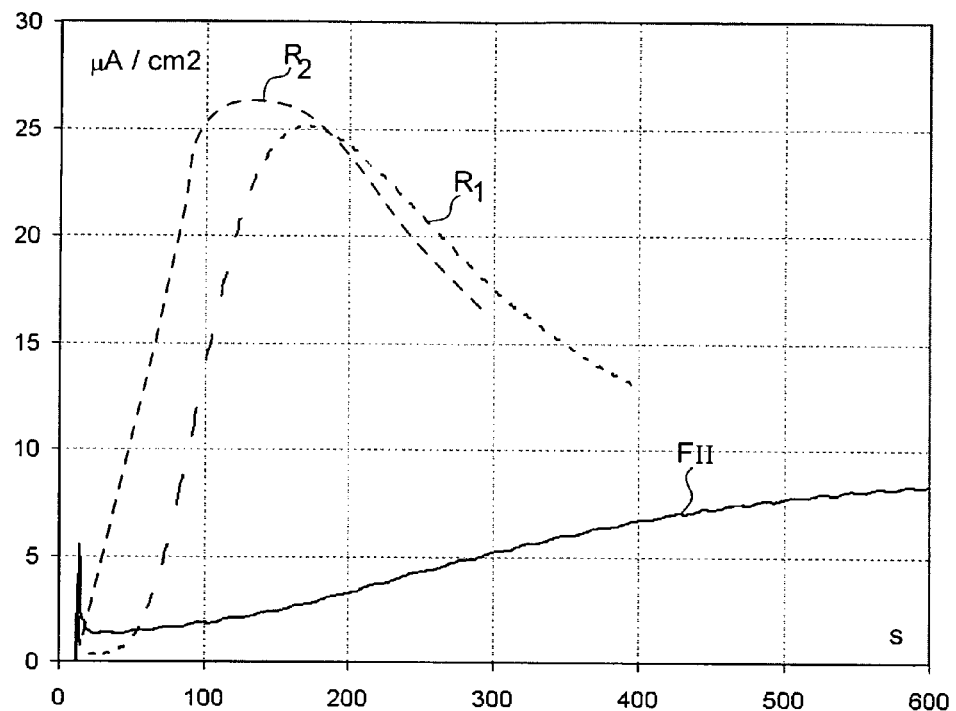
FIG. 3 includes a curve representative of a factor II deficiency.

FIG. 3 shows a graph showing a factor II deficiency, namely prothrombin, in the plasma. It was achieved with a sensor whose working electrode surface is 0.054 cm$^2$ using the oligopeptide TOS-Gly-Pro-Arg-3chloro-4-hydroxyanilide, 2HCL as the substrate.

It is evidently possible to make other choices, both as regards the nature of the substrate and the surface of the working electrode.

The recording was carried out with normal plasma at a constant temperature of 23.5° C. for reference curve $R_1$, and for measuring curve FII. In each case the quantity of sample deposited, or a reference solution, is 10 µl. The measurement was carried out over a period of 10 minutes.

FIG. 3 also shows a second reference curve $R_2$, with normal plasma, at a temperature of 24.5° C., which clearly shows that a difference of only 1° C. causes a significant movement in the curve, and thus in the parameters usually taken into account, in particular:

PH (peak high): maximum signal value
TTP (time to peak): time to reach the peak;
LT (lag time): reaction time
ETP (endogenous thrombin potential) or AUC (area under curve)

Any shift in one of these parameters in relation to the reference value can be interpreted by the practitioner to detect an anomaly in the coagulation phenomenon.

Thus, when curves $R_1$ and FII are compared, measured under in the same conditions and at the same temperature, it can be seen that the PH value is greatly reduced and that the TTP value is considerably increased for FII. This can be interpreted as a prothrombin deficiency or a triggering factor.

Figure 4:
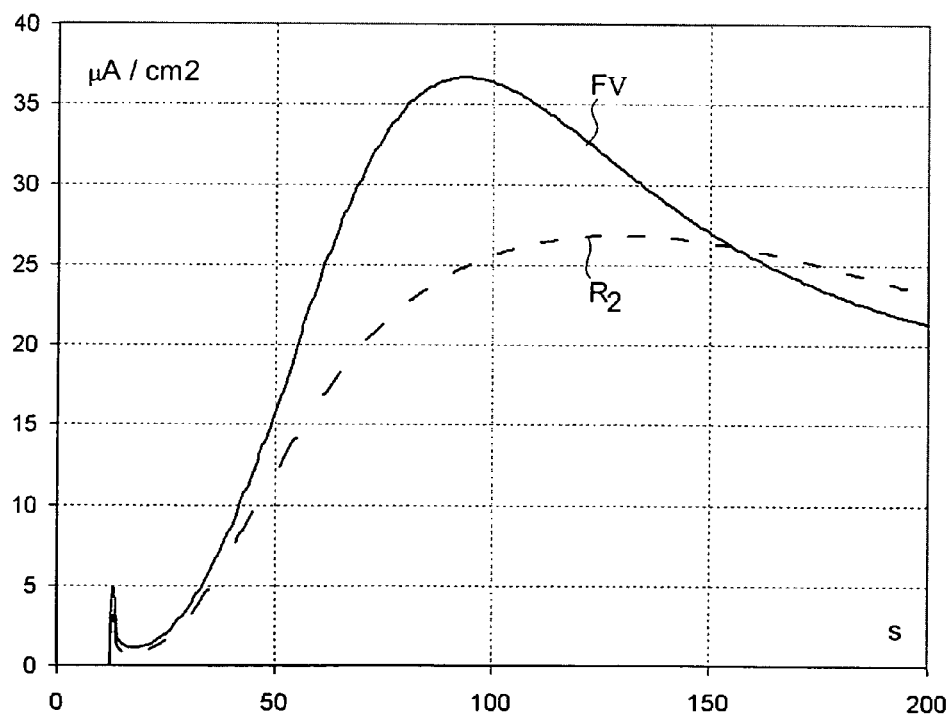
FIG. 4 includes a curve representative of abnormal activity of factor V Leiden.

FIG. 4 shows a graph shown on a different scale, showing the result of a measurement of a plasma sample with a factor V Leiden deficiency. As can be seen in FIG. 4, the PH value is much greater than the reference PH value. A greater TTP value than that of the reference value (curve R1) is observed to reach a slightly greater PH value, which means attenuated factor VII activity.

Figure 5:
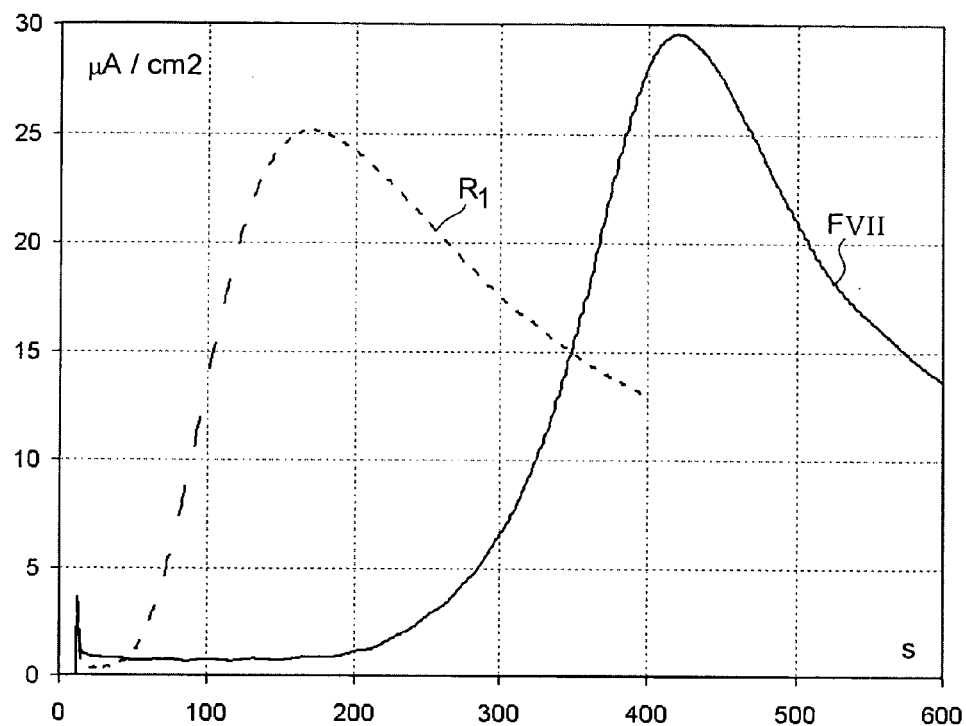
FIG. 5 includes a curve representative of a factor VII deficiency.

FIG. 5 shows, on the same scale as FIG. 3, a graph showing a factor VII deficiency, namely proconvertin, whose presence also contributes to increasing the conversion of prothrombin into thrombin. A larger TTP value than the reference value (curve R1) will be observed to reach an only slightly greater PH value, which means attenuated factor VII activity.

Figure 6:
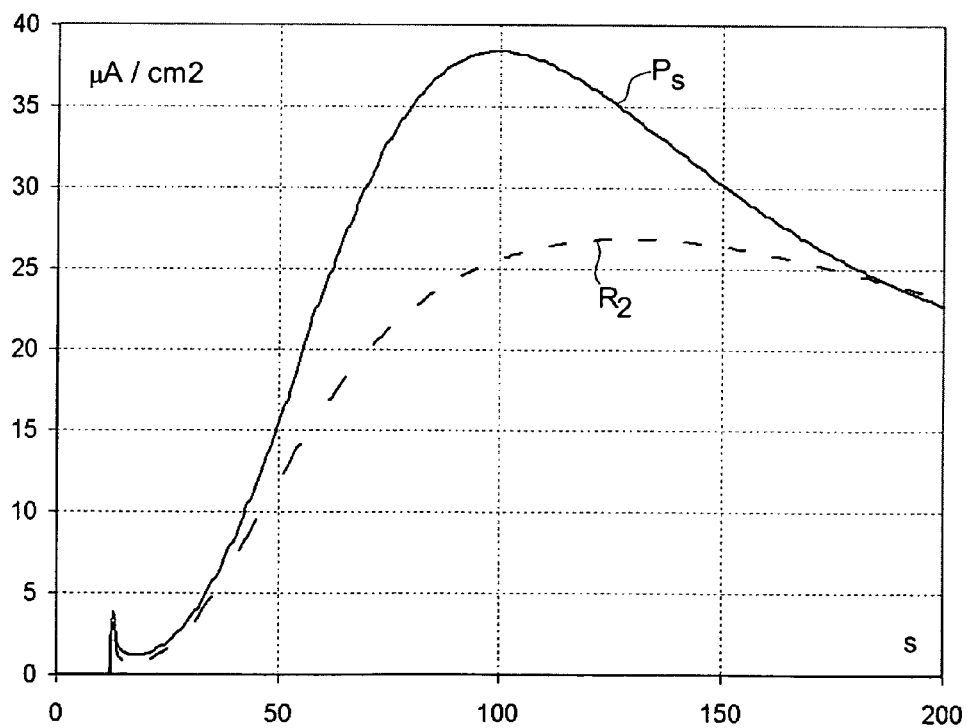
FIG. 6 includes a curve representative of a protein S deficiency.

FIG. 6 shows, on the same scale as FIG. 4, a graph showing a protein S deficiency in the coagulation phenomenon. As can be seen, the TTP value is hardly changed compared to that of the reference value (curve R2) and the corresponding PH value presents a significant increase that can be interpreted as a protein S deficiency.

By using other appropriate specific reagents, it is possible to determine which other factors might be responsible for a coagulation phenomenon anomaly, such as factor VIII or factor IX, a deficiency of which corresponds to a tendency towards haemophilia, protein C, antithrombin III, or lupus anticoagulants.

Likewise, without departing from the scope of the invention, the system could be applied to other bodily fluids by choosing appropriate substrates.

What is claimed is:

1. A system for the electrochemical determination of the evolution of the concentration or activity of at least one proteolytic enzyme for detecting a deficiency or abnormal activity thereof in a small sample of bodily fluid, wherein the system comprises:
   (a) a plurality of assorted electrochemical sensors, each sensor having a shape of a tongue of small dimensions and carrying at least one reference electrode and one working electrode, and a measuring aperture intended to receive the sample of bodily fluid, and a specific reagent for a given proteolytic enzyme is immobilised on the one working electrode of each sensor, wherein the composition of the specific reagent includes at least one chemical substrate, wherein an end link of the chemical substrate can be cut by the proteolytic enzyme to release leaving groups, wherein each sensor of the plurality of assorted sensors includes a material mark corresponding to a specific enzyme;
   (b) a measuring apparatus including at least one connecting slot for receiving a sensor, and the measuring apparatus further includes an electronic circuit, powered by an energy source, that imposes, between the electrodes of the sensors, an electric current whose intensity or voltage may or may not be variable, and the electronic circuit is disposed to receive, in return, an electric signal representative of the release of the leaving groups; and
   (c) an electronic apparatus including software, the electronic apparatus processing a signal transmitted by the measuring apparatus to display on a display screen an indication representative of the release of the leaving groups as a function of time, and
   wherein each material mark comprises a raised portion located along a unique axis of the corresponding sensor and each connecting slot includes a notch complementary to the corresponding raised portion.

2. The system according to claim 1, wherein the electronic circuit of the measuring apparatus is arranged for carrying out a chrono-amperometric determination.

3. The system according to claim 1, wherein the electronic apparatus operates to differentiate the sensors in order to display curves sequentially or in a mosaic on the display screen.

4. The system according to claim 1, wherein the measuring apparatus further includes a closing device for insulating the sensors inserted into said apparatus from the external medium, and a thermoregulation device for keeping the sensors at a determined constant temperature during the entire measurement.

5. The system according to claim 1, wherein the measuring apparatus further includes a thermal probe for measuring the ambient temperature and in that the electronic apparatus operates to select the reference curve as a function of said ambient temperature.

6. The system according to claim 1, wherein the measuring apparatus further includes a secondary display screen for displaying an overall or instantaneous parameter of the measurement being carried out.

7. The system according to claim 1, wherein the measuring apparatus and the electronic apparatus are united in a single operating unit.

8. The system according to claim 1, wherein the volume of the sample of bodily fluid taken is less than 10 µl.

9. The system according to claim 1, wherein the system displays an indication of the measurement carried out on the display screen in graphic or other form.

10. The system according to claim 1, wherein the bodily fluid is blood, particularly whole blood, in which the evolution of the concentration of coagulation factors or conversely coagulation inhibitors is determined to detect any deficiency, or conversely an excess, or abnormal activity.

11. The system according to claim 9, wherein the composition of the specific reagent includes
   (i) at least one oligopeptide substrate;
   (ii) an end link of which can be separated by a coagulation factor to give a leaving group;
   (iii) a thromboplastin; and
   (iv) a buffer medium.

12. The system according to claim 1, wherein said material mark is located at one end of the sensor.

13. The system according to claim 1, wherein the measuring aperture is covered with a cap forming a traverse capillary channel for bringing the bodily fluid to said measuring apparatus.

14. A system for the electrochemical determination of the evolution of the concentration or activity of at least one proteolytic enzyme for detecting a deficiency or abnormal activity thereof in a small sample of bodily fluid, wherein the system includes:
   (a) a plurality of assorted electrochemical sensors, each sensor having a shape of a tongue of small dimensions and carrying at least one reference electrode and one working electrode, and a measuring aperture intended to receive the sample of bodily fluid, and a specific reagent for a given proteolytic enzyme is immobilised on the one working electrode of each sensor, wherein the composition of the specific reagent includes at least one chemical substrate, wherein an end link of the chemical substrate can be cut by the proteolytic enzyme to release leaving groups, wherein each sensor of the plurality of assorted sensors includes a material mark corresponding to a specific enzyme;
   (b) a measuring apparatus including a plurality of connecting slots for receiving the plurality of assorted electrochemical sensors, and the measuring apparatus further includes an electronic circuit, powered by an energy source, that imposes, between the electrodes of the sensors, an electric current whose intensity or voltage may or may not be variable, and the electronic circuit is disposed to receive, in return, an electric signal representative of the release of the leaving groups; and
   (c) an electronic apparatus including software, the electronic apparatus processing a signal transmitted by the measuring apparatus to display on a display screen an indication representative of the release of the leaving groups as a function of time, and
   wherein each mark is formed by a raised portion located along a unique axis of the corresponding sensor and each connecting slot includes a notch complementary to a corresponding raised portion in order to prevent any inversion of the sensors in the slots.

15. The system according to claim 1, wherein the plurality of assorted electrochemical sensors includes a first sensor including a first material mark and a second sensor including a second material mark, wherein the first material mark is located along a central axis of the first sensor and the second material mark is located along an axis offset from a central axis of the second sensor.

16. A system for the electrochemical determination of the evolution of the concentration or activity of at least one proteolytic enzyme for detecting a deficiency or abnormal activity thereof in a small sample of bodily fluid, wherein the system comprises:
   (a) a plurality of assorted electrochemical sensors, each sensor having a shape of a tongue of small dimensions and carrying at least one reference electrode and one working electrode, and a measuring aperture intended to receive the sample of bodily fluid, and a specific reagent for a given proteolytic enzyme is immobilised on the one working electrode of each sensor, wherein the composition of the specific reagent includes at least one chemical substrate, wherein an end link of the chemical substrate can be cut by the proteolytic enzyme to release leaving groups, wherein each sensor of the plurality of assorted sensors includes a material mark corresponding to a specific enzyme;
   (b) a measuring apparatus including at least one connecting slot for receiving a sensor, and the measuring apparatus further includes an electronic circuit, powered by an energy source, that imposes, between the electrodes of the sensors, an electric current whose intensity or voltage may or may not be variable, and the electronic circuit is disposed to receive, in return, an electric signal representative of the release of the leaving groups; and
   (c) an electronic apparatus including software, the electronic apparatus processing a signal transmitted by the measuring apparatus to display on a display screen an indication representative of the release of the leaving groups as a function of time, and
   wherein each mark comprises a raised portion located along a unique axis of the corresponding sensor and each connecting slot includes a notch complementary to a corresponding raised portion in order to prevent any inversion of the sensor, wherein the plurality of assorted electrochemical sensors includes a first sensor including a first material mark and a second sensor including a second material mark, wherein the first material mark is located along a central axis of the first sensor and the second material mark is located along an axis offset from a central axis of the second sensor,
   wherein the first sensor includes a first chemical substrate and the second sensor includes a second chemical substrate that is a different substrate than the first chemical substrate.

17. The system according to claim 16, wherein the offset axis of the second material mark is located to the right of the central axis of the second sensor, and the plurality of assorted electrochemical sensors further includes a third sensor including a third material mark that is located along an axis offset to the left from a central axis of the third sensor.

18. The system according to claim 14, wherein the plurality of assorted electrochemical sensors includes a first sensor including a first material mark and a second sensor including a second material mark, wherein the first material mark is located along a central axis of the first sensor and the second material mark is located along an axis offset from a central axis of the second sensor.

19. The system according to claim 18, wherein the first sensor includes a first chemical substrate and the second sensor includes a second chemical substrate that is a different substrate than the first chemical substrate.

20. The system according to claim 19, wherein the offset axis of the second material mark is located to the right of the central axis of the second sensor, and the plurality of assorted electrochemical sensors further includes a third sensor including a third material mark that is located along an axis offset to the left from a central axis of the third sensor.

21. The system according to claim 1, wherein the measuring apparatus recognizes the material mark on the sensors to determine the proteolytic enzyme being measured.

\* \* \* \* \*